US005797871A

United States Patent [19]
Wolfinbarger, Jr.

[11] Patent Number: 5,797,871
[45] Date of Patent: Aug. 25, 1998

[54] ULTRASONIC CLEANING OF ALLOGRAFT BONE

[75] Inventor: Lloyd Wolfinbarger, Jr., Norfolk, Va.

[73] Assignee: LifeNet Research Foundation, Virginia Beach, Va.

[21] Appl. No.: 646,519

[22] Filed: May 7, 1996

Related U.S. Application Data

[63] Continuation-in-part of Ser. No. 646,520, May 7, 1996, and Ser. No. 395,113, Feb. 27, 1995, Pat. No. 5,556,379, which is a continuation-in-part of Ser. No. 293,206, Aug. 19, 1994, abandoned.

[51] Int. Cl.[6] .................................................. A61M 31/00
[52] U.S. Cl. ........................... 604/49; 128/898; 623/16; 134/61
[58] Field of Search .......................... 128/898; 604/28, 604/48, 49; 600/36; 623/16; 435/1, 2, 67, 268; 134/61

[56] References Cited

U.S. PATENT DOCUMENTS

| | | | |
|---|---|---|---|
| 4,020,183 | 4/1977 | Asculai et al. | 424/341 |
| 4,169,123 | 9/1979 | Moore et al. | 422/29 |
| 4,207,689 | 6/1980 | Romera-Sierra et al. | 35/20 |
| 4,258,722 | 3/1981 | Sessions et al. | 128/753 |
| 4,315,919 | 2/1982 | Shanbrom | 424/177 |
| 4,366,822 | 1/1983 | Altshuler | 128/752 |
| 4,412,985 | 11/1983 | Shanbrom | 424/78 |
| 4,456,589 | 6/1984 | Holman et al. | 424/95 |
| 4,526,751 | 7/1985 | Gartner | 422/37 |
| 4,553,974 | 11/1985 | Dewajnee | 8/94.11 |
| 4,637,931 | 1/1987 | Schmitz | 424/78 |
| 4,678,470 | 7/1987 | Nashef et al. | 623/16 |
| 4,695,536 | 9/1987 | Lindstrom et al. | 435/1 |
| 4,801,299 | 1/1989 | Brendel et al. | 623/1 |
| 4,891,221 | 1/1990 | Shanbrom | 424/101 |
| 4,923,677 | 5/1990 | Simon et al. | 422/37 |
| 4,946,792 | 8/1990 | O'Leary | 435/268 |
| 4,975,526 | 12/1990 | Kuberasampath et al. | 530/350 |
| 4,994,030 | 2/1991 | Glowczewskie et al. | 604/84 |
| 5,037,437 | 8/1991 | Matsen, III | 623/16 |
| 5,041,055 | 8/1991 | Roth | 452/140 |
| 5,047,030 | 9/1991 | Draenert | 606/65 |
| 5,095,925 | 3/1992 | Elledge et al. | 134/61 |
| 5,106,626 | 4/1992 | Parsons et al. | 424/423 |
| 5,118,512 | 6/1992 | O'Leary et al. | 424/549 |
| 5,120,656 | 6/1992 | O'Leary et al. | 435/268 |
| 5,133,756 | 7/1992 | Bauer et al. | 623/16 |
| 5,167,961 | 12/1992 | Lussi et al. | 424/423 |
| 5,186,945 | 2/1993 | Shanbrom | 424/529 |
| 5,192,282 | 3/1993 | Draenert | 606/65 |
| 5,333,626 | 8/1994 | Morse et al. | 604/48 |
| 5,454,815 | 10/1995 | Geisser et al. | 606/85 |
| 5,513,662 | 5/1996 | Morse et al. | 128/898 |

FOREIGN PATENT DOCUMENTS

| | | |
|---|---|---|
| 952189 | 8/1982 | U.S.S.R. . |
| 964545 | 7/1964 | United Kingdom . |
| WO 97/07389 | 2/1997 | WIPO . |

OTHER PUBLICATIONS

Sattar et al., "Survival and Disinfectant Inactivation of the Human Immunoeficiency Virus: A Critical Review", RID 1991; 13 (May–Jun.), pp. 430–447.

Exact. excerpts from "Product Specification, Discription, Patent Application & Supporting Documentation", by EXOxEMIS, Inc., Feb. 1991.

(List continued on next page.)

*Primary Examiner*—Michael Buiz
*Assistant Examiner*—Deborah Blyveis
*Attorney, Agent, or Firm*—Jones & Volentine, L.L.P.

[57] ABSTRACT

The present invention is directed to a method for cleaning cadaveric donor bone to produce bone grafts suitable for transplantation into a human, as well as the bone grafts produced thereby. The present method involves removing bone marrow potentially containing bacteria, virus or fungi, from the donor bone by sonicating the bone in a solvent containing one or more detergents to produce bone grafts essentially free from bone marrow, as well as bone grafts essentially free from any detectable bacterial, fungal, or viral contamination.

25 Claims, 5 Drawing Sheets

OTHER PUBLICATIONS

Klebanoff et al., "Virucidal Activity of H2O2-generating Bacteria; Requirement for Peroxidase and Halide", Dept. of Medicine, University of Washington School of Medicine, Seattle Washington, Sep. 24, 1973.

"DMIN Aseptic Tissue Demineralization", a product brochure from Osteotech, Inc. 1993.

"Maximum Security for You and Your Parent", a product brochure regarding VIP Bone, from Cryolife, Inc., Feb. 12, 1992.

"The Virucidal Capacity of a Surfactant/Iodophor–Based Viral Inactivation Process for Bone Allografts", a report of studies designed and funded by Cryolife, Inc., undated.

Withrow et al., "Evaluation of the Antiretroviral Effect of various Methods of Sterilization/Preserving Cortiocancellous Bone", presented at the 36th Annual Meeting, Orthopaedic Research Society, Feb. 5–8, 1990, New Orleans, Louisianna, Transactions of the Orthopaedic Research Society, 16, 1990, pp. 226.

Garrison et al., "Comparison of Bacterial Contimation of Cadaveric Bone Allograft Collected Under Operation Room and Morgue Condition with and without the use of Decontaminating Process", presented at the Second Congress of the European Association of Tissue Bank, Athens, Greece, May 1993.

Morse, "A New Surfactant/Iodophor–Based Viral Inactivation Process (VIP) for Preparation of Bone Allografts", presented at the 16th Annual Meeting of the American Association of Tissue bank, San Diego, Aug. 1992.

"Improve Performance of Your Immunoassay Systems and Immunodiagnostics Kits", a product brochure by Medicine & Applied Sciences, Inc., undated.

"Viral Inactivation Agent for Blood Samples", an article referring to an Oct. 1990 issue of *American Clinical Laboratory* entitled an Antiviral Agent for General Use in Biological Samples.

*Virginia Tissue Bank Procedure Manual*, Section 5.9.4.5, Copyright registered on Aug. 6, 1986.

Buck et al., "Human Immunodeficiency Virus Cultured From Bone. Implications for Transplantation", Clinical Orthopaedics and Related Research, No. 251, 1990.

*Navy Tissue Bank, Tissue Bank Coordinator Manual 10*, "Procurement of Deep Tissues and Bones", p. 9. (undated).

Shutkin, "Homologous–Serum Hepatitis following the Use of Refrigerated Bone–Bank Bone", The Journal of Bone and Joint Surgery, vol. 16–1, No. 1, 1954.

Hyatt et al., "Bone Grafting. The Procurement, Storage, and Clinical Use of Bone Homografts", The American Academy of Orthopaedic Surgeons, Ann Arbor, U.S.A., 1957.

"Transmission of HIV through Bone Transplantation: Case Report and Public Health Recommendations", Morbidity and Mortality Weekly Report, vol. 37, No. 39, 1988.

Kakaiya et al., "Tissue Transplant–Transmitted Infections", Transfusion, vol. 31, No. 3, 1991.

Tomford et al., "A Study of the Clinical Incidence of Infections in the Use of Banked Allograft Bone", The Journal of Bone and Joint Surgery, vol. 63–A, No. 2, 1981.

Furlini et al., "Antibody Response to Human Immunodeficiency Virus after infected Bone Marrow Transplant", Eur. J. Clin, Microbiol. Infect. Dist., vol. 7, 1988.

Lord et al., "Infection in Bone Allografts. Incidence, Nature, and Treatment", The Journal of Bone and Joint Surgery, vol. 70–A, No. 3, 1988.

Bonfiglio et al., "The Immune Concept: Its Relation To Bone Transplantation", Annals New York Academy of Sciences, 1955.

Doppelt et al., "Operational and Finacial Aspects of A Hospital Bone Bank", The Journal of Bone Joint Surgery, vol. 63–A, No. 9, 1981.

Dirschi et al., "Topical Antibiotic Irrigation in the Prophylaxis of Operative Wound Infections in Orthopedic Surgery", Orthopedic Infection, vol. 22, No. 3, Jul. 1991.

Reynolds et al., "Clinical Evaluation of the Merthiolate Bone Bank and Homogenous Bone Grafts", The Journal of Bone and Joint Surgery, vol. 33–A, No. 4, 1951

"Med Clean Mark II", a product brochure by Advanced International Marketing for a unit which includes a pressurized stream of water for bone debridement. (undated).

U.S. Department of Health and Human Services/Public Health Service, "Transmission of HIV Through Bone Transplantation: Case Report and Public Health Recommendations," Morbidity and Morality Weekly Report, 37, 1988. pp. 597–599.

Mellonig, J. T. et al., "HIV Inactivation in a Bone Allograft", J. Periodontology, Dec. 1992, Vol. 63, pp. 979–983.

ULTRASONIC CLEANING OF ALLOGRAFT BONE

BACKGROUND OF THE INVENTION

This application is a continuation-in-part of co-pending U.S. application Ser. No. 08/646,520 filed May 7, 1996 entitled "A Recirculation Method for Cleaning Essentially Intact Bone Grafts Using Pressure Medicated flow of Solvents and Bone Grafts Produced Thereby", and this application is a Continuation-in-Part of U.S. application Ser. No. 08/395,113 filed Feb. 27, 1995 now U.S. Pat. No. 5,556,379 which is a Continuation-in-Part of U.S. application Ser. No. 08/293,206 filed Aug. 19, 1994, now abandoned, all of which we incorporated by reference herein in their entirety.

FIELD OF THE INVENTION

The present invention relates to a method for cleaning bone grafts to produce bone grafts suitable for transplantation into a human as well as the cleaned bone grafts produced thereby. The invention possesses the attributes of being usable on a large number of essentially Intact bone grafts, including but not limited to: femur, femur head, distal end of femur, proximal end of femur, fibula, tibia, ilia, mandibular, humorous, radius, ulna, vertebrae, ribs, scapula, foot bones and hand bones, prior to subsequent processing into small specific cut-bone grafts and of being usable on small cut-bone grafts, including but not limited to iliac crest wedges, Coward dowels, ribs, cancellous cubes, fibular struts, not cleaned prior to cutting. The process involves the use of ultrasonic cleaning in the removal of bone marrow from the interstitial lumen and cancellous bone space of large bone grafts by causing a flow of solvent through the cartilaginous ends of bone and out through lumen and cancellous bone space by use of a vacuum in the presence of ultrasonic cavitation in detergent solution(s). The process further involves the use of ultrasonic cleaning of smaller cut grafts in a commercially available ultrasonic cleaner using cavitation in the presence of detergents to disrupt and disperse residual bone marrow and bone marrow elements in the cancellous bone space of the small cut grafts. The solvent includes a combination of solutes which improve solvent penetration into and through the bone graft and increases the solubility of bone marrow, facilitating its removal from the large, essentially Intact, bone graft and small cut-bone grafts.

DISCUSSION OF BACKGROUND INFORMATION

Human bone obtained from cadaveric donors is typically procured under sterile conditions in an operating suite environment of local hospitals. The bone is stored frozen until it is further processed into small grafts under similar sterile conditions, or under clean-room conditions. Procurement and processing of human tissues is typically performed by groups certified by the American Association of Tissue Banks under standard operating procedures for the processing of each specific bone graft. Large bones such as the femur are thawed and debrided of excess tissue prior to being cut into smaller grafts. Processing of the smaller grafts includes cleaning of bone marrow from the cancellous bone spaces.

Cleaning of bone marrow from small bone grafts has been described in the scientific literature and in brochures and documents made public by groups involved in the procurement and processing of human tissues. A for-profit public corporation, Cryolite, Inc. (Mariti, Ga.) promotes a patented, U.S. Pat. No. 5,333,626, bone cleaning process designated as VIP™ (Viral Inactivation Process) and claims that the process provides "Cleaner bone through mechanical removal of debris and tissue such as bone marrow, lipids and blood components" and "Safer bone through inactivation of pathogens such as HBV and HIV (greater than 5-log kill) as well as bacteria and fungi" (Cryolite Orthopedics, Inc. brochure 12 Feb. 1992).

A second, for-profit corporation, Osteotech, Inc., Shrewsbury, N.J., describes a bone graft cleaning process called Permein™ ("a combination of ethanol and non-ionic detergent"; Mellonig, J. T., Prewett, A. B., and Moyer, M. P. J. Periodontol. December 1992, vol. 63, pp 979–983). This process involves the use of a solution of ethanol and detergent to clean bone grafts.

A not-for-profit organization, LifeNet Research Foundation developed a technology for cleaning large essentially intact bone grafts using a vacuum mediated flow of solutions for removing bone marrow and bone marrow elements from bone (a continuation-in-part of application Ser. No. 08/395, 113 which is a continuation in part of Ser. No. 08/293,206 in the name of Lloyd Wolfinbarger, Jr. entitled "Process for Cleaning Large Bone Grafts and Bone Grafts Produced Thereby) which is incorporated herein by reference in its entirety.

SUMMARY OF THE INVENTION

An object of the present invention is to provide a means of removing bone marrow from the luminal and cancerous bone spaces in essentially intact, bone grafts and small cut-bone grafts.

In this regard, it is a further object of the invention to provide essentially intact bone graft material, essentially free of residual bone marrow, for use in the preparation of small bone grafts. Essentially intact bone grafts with minimal residual bone marrow offer additional advantages in that removal of bone marrow, which may harbor potential viral particles and/or viral genomes integrated into the genomes of specific cell types present in the bone marrow, reduces the potential for transmission of infective agents such as bacteria and viruses, especially the human immunodeficiency virus (HIV) in that cells capable of harboring this virus are abundant in bone marrow and their removal from essentially intact bone grafts also reduces the bioburden of viruses which may be present within the bone marrow cells removed.

Another object of this invention is to use alcoholic and soluble amphophil (detergent) solutions in the removal of bone marrow from bone grafts. Alcohol and detergents have been demonstrated to be virucidal towards enveloped viruses such as the HIV and hepatitis and certain bacteria and to enhance cavitation associated with ultrasonic cleaners. Alcohol and detergent solutions also offer advantages of enhancing solubilization of bone marrow, reducing surface tension properties of aqueous solutions, and inactivating viruses and bacteria. Ultrasonic cleaners offer advantages of cavitation events which facilitate disruption and breakdown of soft tissues at the microscopic level.

Another object of this invention is to use ultrasonic cleaning to cavitate the alcoholic and soluble amphophil (detergent) solutions facilitating the removal of bone marrow and bone marrow elements from essentially intact bone grafts and/or small bone grafts.

A further object of this invention is to provide methods for removing bone marrow from bone grafts prior to their being cut into smaller bone grafts. The use of vacuum induced flow of solvent through the bone grafts in the presence of ultrasonic cavitation offers the advantages of reducing the solubility of dissolved air in the fluid present within the bone marrow enhancing cavitation in the cleaning solution, i.e., an improvement over the simple use of ultrasonic cleaning in the presence of dissolved gases in the cleaning solutions, of causing a movement of solvent solubilized bone marrow in the direction of the vacuum source, of minimizing structural damage to the cancellous bone by using minimally invasive cleaning methods, and of permitting containment of the aspirated bone marrow/solvent in containers which may be safely handled and disposed without exposure of the processing personnel. Use of hypotonic solutions induces bone marrow cell swelling and by reducing the solubility of dissolved air in the fluid present in the bone with vacuum application to the bone, dissolved air comes out of solution forming gas bubbles which if formed within cells in the bone marrow will enhance rupture of the already swollen cells, with subsequent loss of cytoplasmic materials.

Cavitation induced fragmentation and solubilization of cells and acellular materials is enhanced in the absence of dissolved gases in aqueous solution. Since dissolved air (gases) cushions the force of cavitation, this aspect of the invention improves on the efficiency of ultrasonic mediated cleaning of the bone grafts. Ultrasonic cleaning involves the formation of vacuum bubbles as a result of cavitation and in the presence of dissolved air in the cleaning solution, the vacuum bubbles will be filled with gas, cushioning the force of cavitation. The movement of solvent in the direction of the vacuum source will result in the continual exchange of solvent with the result that temperatures within the bone being cleaned can be more easily controlled and solubilized bone marrow is removed and bone marrow which has not been solubilized will be exposed to additional fresh solvent. Thus the continual replacement of solvent in the presence of cavitation will reduce the need for greater concentrations of solubilization enhancing components.

Detergents are amphophil compounds which facilitate solubilization of relatively insoluble lipids present in, for example, bone marrow, yet at higher concentrations tend to form micellar structures (Helenius, A. and Simons, K. Solubilization of Membranes by Detergents, Biochim. Biophys. Acta 415 (1975) 29–79). The formation of micellar structures tend to limit the effective concentration range for detergent solutions and thus soaking of bone in a given volume of detergent solution may not be totally effective in that the absolute amount of detergent present is limited and if the amount of lipid material to be solubilized exceeds the solubilization capability of the detergent present, lipid solubilization will not be complete. By continually changing the detergent solution over time, it becomes possible to completely solubilize all solubilizable lipid present in a bone graft.

Restricted flow of solvent through the cartilaginous ends of the bone will minimize mechanical and/or structural damage to the cancellous bone by causing a slow flow rate of solvent through the trabecular bone space occupied by bone marrow. The containment of aspirated bone marrow/solvent is made possible by use of disposable containers for collection of the aspirate. In addition, it becomes possible to add strong viral/bacterial inactivators, for example sodium hypochlorite, to the disposable collection containers to further inactivate potential pathogenic and/or biohazardous biomaterials. Filters between the vacuum source and the collection containers further prevents the potential spread of biohazardous materials. The use of prior art procedures to remove bone marrow involves the use of pressurized flow of solution as a rapidly moving stream which dislodges bone marrow by impact of the solvent on the bone graft. Such procedures tend to generate aerosols of tissue and solvent which can be hazardous to processing personnel. The present invention virtually eliminates this hazard.

Ultrasonic cleaners are extensively used in cleaning glass tubes, metal instruments, filters, etc. (Branson Ultrasonics Corporation brochure). Ultrasound is sound transmitted at frequencies beyond the range of human hearing. Ultrasonic energy generated by piezoelectric transducers at a rate of 55,000 time per second creates cavitation, which is the mechanism for ultrasonic cleaning. Cavitation consists of the formation and collapse of countless tiny cavities, or vacuum bubbles, in the liquid. The energy produces alternating high and low pressure waves within the liquid of a tank. The liquid is compressed during the high pressure phase of the wave cycle, then pulled apart during the low pressure phase. As the pressure in the liquid is reduced during the low pressure phase, cavities grow from microscopic nuclei to a maximum critical diameter. During the subsequent high pressure phase they are compressed and implode. The energy is powerful, but safe for parts because it is localized at the microscopic, i.e., cellular, scale. Factors affecting the strength of cavitation are temperature, optimally between 120° F. and 140° F., surface tension, optimally detergents or other agents which reduce surface tension are optimal, viscosity (medium vapor pressure is most conducive to ultrasound activity), and density (where high density creates intense cavitation with greater implosive force).

A yet further object of the invention is to provide mechanical devices which permit attachment of vacuum lines to the various large bone grafts being cleaned by the process of vacuum induced solvent flow, which permit attachment of solvent containers around the bone grafts being cleaned, and to permit the collection and containment of aspirate materials from the bone grafts. These mechanical devices can be sterilized by a variety of procedures, for example autoclaving, and form tight seals with the bone grafts being cleaned.

BRIEF DESCRIPTION OF THE DRAWINGS

FIG. 1 illustrates a flow chart diagram of a preferred embodiment of the present method for producing a cleaned bone graft using sonication and agitation.

FIG. 2 illustrates the present method for producing a cleaned bone graft using a negative pressure mediated flow of solvent.

FIG. 3 illustrates an example of changes in absorbance with volume of detergent drawn through a typical bone graft. Concentrations of proteins (microgram/ml of eluent) eluting from porcine proximal femurs being flushed with deionized/distilled water (+), 0.01X Allowash™ in Dulbecco's Phosphate Buffered Saline (DPBS) (Δ), and 0.01X solution in a 30% (vol:vol) ethanolic solution in deionized/distilled water (X). Flushing procedure utilizes peristaltic pump induced flow of solutions and eluent materials are collected as 15 ml volumes using a fraction collector. Aliquots of eluent are assayed for protein concentrations using a protein assay. The data included in this figure is used only to illustrate the relative quantities of bone marrow solubilized by the different solutions shown and is not intended to document bone marrow solubilization as described in the patent application.

FIG. 4 illustrates the present method using a negative pressure mediated flow of solvent to clean a proximal end of a femur.

FIGS. 5 and 5A illustrate the cleaning of a femur head.

DETAILED DESCRIPTION OF THE PREFERRED EMBODIMENTS

Figure 1:
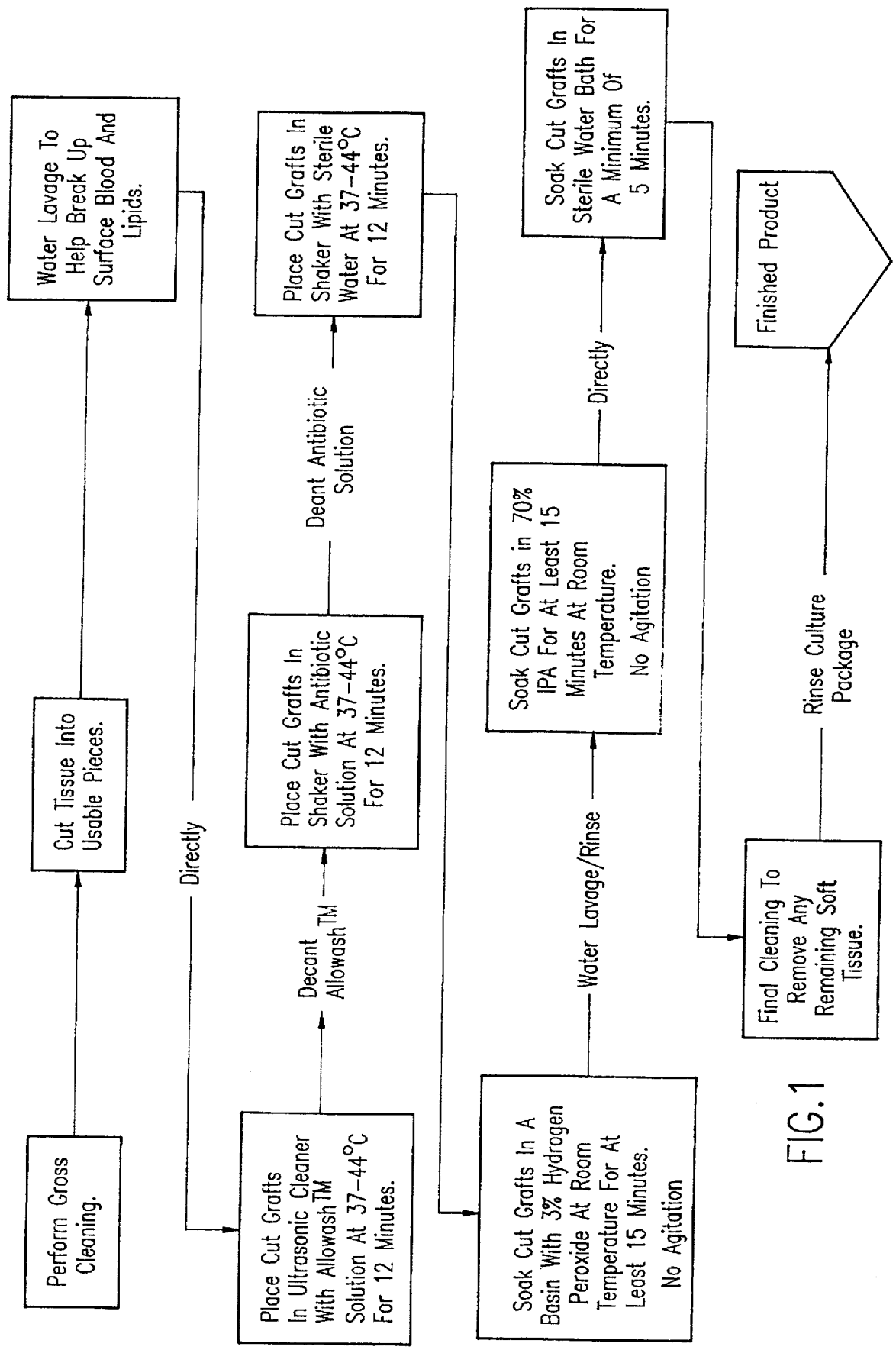
FIG. 1.

Definitions. The below definitions serve to provide a clear and consistent understanding of the specifications and claims, including the scope to be given such terms.

Allowash™ Solution. By the term "Allowash™ solution" is intended those (compositions) disclosed in co-pending U.S. patent application Ser. No. 08/620,856 incorporated herein by reference. Examples of suitable Allowash™ compositions include: A cleaning composition containing essentially about 0.06 wt % polyoxgethylene-4-lauryl ether; about 0.02 wt % poly (ethylene glycol)-p-nonyl-phenyl-ether; about 0.02 wt % octylphenolethyleneoxide and endotoxin free deionized/distilled water.

Bone Graft. By the term "Bone Graft" is intended any bone or piece thereof obtained from a cadaver donor, for example any essentially intact bone including for example the femur, tibia, ilia, humorous, radius, ulna, ribs, whole vertebrae, mandibula and/or any bone which can be retrieved from a donor with minimal cutting of that bone for example, one half of an ulna, a femur cut in half to yield a proximal half and a distal half, and/or at least a substantial portion of a whole bone, i.e. at least one-quarter of a whole bone; and/or any small cut pieces of bone, for example, iliac crest wedges, ground bone, Coward dowels, cancellous cubes, and/or fibular struts.

Mild agitation. By the term "mild agitation" is intended agitation achieved through the use of a gyrator shaker or means to achieve a similar result, including, for example: pulsatile lavage wherein induced currents in the solution impact the surface of bone and annoited soft time.

Vigorous Agitation. By the term "vigorous agitation" is intended agitation achieved through the use of a commercial paint can shaker or other means which achieve a similar result including, for example, high pressure pulsatile lavage wherein induced currents in the solution impact the surface of bone and annoited soft tissue.

Pressure Mediated Flow of Solvent. By the term "pressure mediated flow of solvent" is intended for the purposes of the present invention means a flow of solvent induced by positive or negative pressure.

Cleaning Container. By the term "cleaning container" is intended for the purpose of the present invention any rigid or deformable container of a size sufficient to contain the bone graft being processed. This sterile cleansing container may be the "beaker" of a Branson ultrasonic cleaner, for example, Models 1210, 2210, 3210, etc. as size of the bone graft dictates, capable of operating at between 20 KHz and 50 KHZ at temperatures up to 69°±5° C.

Detergent. By the term "detergent" is intended any agent which through a surface action that depends on it possessing both hydrophilic and hydrophobic properties and/or exerts oil-dissolving (cleansing) and/or antibacterial and/or antiviral effects, and can include but is not limited to: anionic detergents, cationic detergents, acridine derivatives, long-chain aliphatic bases or acids, etc.

Ultrasonic Cleaner. By the term "ultrasonic cleaner" is intended any ultrasonic cleaning device capable of operating at: from 20 KHZ to 50 KHz, preferably from about 40 KHZ to about 47 KHZ, and includes, for example, Branson ultrasonic cleaner model nos.: 1210, 2210, 3210, 5210 and 8210; or any similar ultrasonic cleaner.

Bone Marrow. By the term "bone marrow" is intended for the purposes of the present invention the highly cellular hematopoietic connective tissue filling the medullary cavities and spongy epiphyses of bones which may harbor bacterial and/or viral particles and/or fungal particles.

Decontaminating Agent. By the term "decontaminating agent" is intended one or more agents which remove or inactivate/destroy any infectious material potentially present in the bone marrow of a bone graft, for example, such materials including but not limited to: bacteria, virus, and/or fungi; with such decontaminating agents including, for example, but not limited to one or more of the following: an antibacterial agent; an antiviral agent; an antimycotic agent; an alcohol for example, methyl, ethyl, propyl, isopropyl, butyl, and/or t-butyl; trisodium phosphate; sodium hydroxide; hydrogen peroxide; and/or any detergent.

Negative Pressure. By the term "negative pressure" is intended for the purposes of this invention a pressure below atmospheric pressure, i.e., less than one atmosphere.

Positive Pressure. By the term "positive pressure" is intended for the purposes of this invention a pressure at or above one atmosphere, i.e., greater than or equal to one atmosphere.

Essentially Closed System. By the term "essentially closed system" is intended for the purposes of the present invention, a system which prevents the potential spread of any potentially biohazardous materials present in bone marrow, i.e. bacterial and/or viral and/or fungal particles; for example, a system whereby aspirated bone marrow and solvent is contained and thus does not come into contact with processing personal and whereby aerosols of tissues are not generated.

Essentially Free From. By the term "essentially free from" is intended a bone graft where the material removed (i.e., bone marrow, viral, fungal, and/or bacterial particles) from the bone graft is not detectable using detection means known in the art at the time of filing of this application.

Essentially Intact Bone Graft. By the term "essentially intact bone graft" is intended for the purposes of the present invention any whole bone including, for example, the femur, tibia, ilia, humorous, radius, ulna, ribs, whole vertebrae, mandibular, and/or any bone which can be retrieved from a donor with minimal cutting of that bone, for example, one half of an ulna, a femur cut in half to yield a proximal half and a distal half, and/or at least a substantial portion of a whole bone, i.e., at least one-quarter of a whole bone.

Solvent. By the term "solvent" is intended for the purposes of the present invention, a liquid cleaning composition capable of: facilitating the solubilization of lipid, facilitating bone marrow removal, inactivating viral and/or bacterial particles, and/or disrupting cell membranes, which may contain, but is not limited to, one or more of the following: sterile water; saline; a detergent; an alcohol, for example, ethanol and/or isopropanol, solvents, a combination of solutes desired to facilitate solubilization of bone marrow, for example, Allowash™ solution disclosed in co-pending patent application Ser. No. 08/620,856 herein incorporated by reference; chelating agent; virucidal agent; bacteriocidal agent; antimycotic agent; sodium hydroxide or similar strong base, organic and/or inorganic acid and hydrogen peroxide.

II. Cleaning of Essentially Intact Bone Grafts

A preferred embodiment of the present invention involves a process for cleaning essentially intact bone grafts. First, bone materials procured from cadaveric donors are thawed.

Following thawing under sterile conditions at room temperature, the bone may be debrided of external soft tissues. This debridement can include removal of excess cartilaginous tissues on the proximal and distal ends of bones at their points of articulation. Soft tissue debridement is of use if it is desired to assess the quality of the bone prior to further processing, however, debridement is not an essential element of the bone cleaning technology. The bone is attached to the vacuum source and placed into the solvent solution in an appropriate container, for example, a sterile basin or the tank of a commercially available ultrasonic cleaner, for example, Branson models 1210, 2210, 3210, 5210, or 8210—each of which hold essentially larger and larger volumes of cleaning solution. Preferably, the ultrasonic cleaner operates at (at) least 20 KHz, more preferably 30 KHz to 50 KHz, and most preferably 40 KHz to 47 KHz. The container is closed around the vacuum line or point of attachment to the bone graft to restrict movement of cleaning solution and a vacuum is applied to the system. The ultrasonic cleaner is then turned on with confirmation of cavitation performed. As solvent solution is drawn through the bone graft, it is collected in the disposable container. Solutions in the container can be changed by addition of new solution through a filling port. Co-pending application Ser. No. 08/646,519 filed May 7, 1996 entitled "A Recirculation Method for Cleaning Essentially Intact Bone Grafts Using Pressure Mediated Flow of Solvents and Bone Grafts Produced Thereby" is incorporated herein in its entirety and describes in detail methods for cleaning essentially intact bone grafts.

The vacuum source used to draw solution through the bone grafts will be between 15 and 35 inches Hg with the preferred range being between 20 and 30 inches Hg. The actual vacuum level is adjusted such that the flow rate of solution through the bone graft does not occur so rapidly that the bone marrow is not effectively solubilized, but rapidly enough to effectively remove solubilized bone marrow. Flow rates of solvent should range between 8 and 32 mls per minute with the preferred rates being between 15 and 25 mls per minute.

The first solvent to be drawn through the bone graft will consist of a sterile mixture of detergent and/or alcohol, for example, ethanol or isopropanol in endotoxin-free deionized/distilled water. Detergents utilized may include, but not be restricted to, ionic and/or nonionic detergents such as polyoxyethylene alcohols (Brij series, Lubrol W, etc.), polyethylene glycol p-isooctylphenylethers (Triton X series), Nonidet P40/Igepal CA 630, nonoxynol 9Igepal CO 630, polyoxyethylene nonylphenol (Triton N series, Surfonic N series, Igepal CO series), polyoxyethylene sorbitol esters (Tween series, Emasol series), the formulation known as Allowash™ Solution (LifeNet Research Foundation, Virginia Beach, Va.) in concentrations ranging between 0.001 wt % to 2 wt % with the preferred concentrations being between 0.01 and 0.5 wt %. The concentration of alcohol which may be used in the first solution ranges between 5% and 95% (volume to volume) with the preferred range being between 10 and 30% (volume to volume).

The second solvent to be drawn through the bone graft will consist of endotoxin-free deionized/distilled water, alcoholic solutions of water, or isotonic saline in endotoxin-free deionized/distilled water. The second solution may be added to the container, used to contain the first solution, using the filling port. During addition of the second solvent to the container, the vacuum should be shut off in order to facilitate filling of the container. Ultrasonic cleaning may be used during this second solvent process, however it is generally not necessary since the first solvent processing is maximally effective in facilitating removal of bone marrow and bone marrow elements. The purpose of the second solvent is to reduce the amount of the first solution in the bone graft and/or to deliver additional agents to be used in processing of the essentially intact bone graft. For example, addition of ethanol or isopropanol (50% to 100%, vol to vol) to the washing solvent would serve to reduce bacterial, fungal, and/or viral contaminants which might be present in the bone graft. The use of absolute (100%) ethanol in the second solution would further serve to dehydrate the bone, reducing subsequent times needed for freeze-drying. Since the flow of solvent through the bone graft will be less restricted during the flushing with the second solvent, the level of vacuum used should be appropriately reduced to maintain an appropriate flow rate between 10 and 15 ml per minute. The volume of the second solvent may vary depending on the concentration of detergent and/or ethanol used in the first solvent, but in general should approximate a volume 10-fold greater than the volume of the bone graft being processed.

Following completion of flushing of bone graft with the second solution, the bone graft may be removed from the sterile container and processed into smaller bone grafts via procedures previously established for the production of such grafts.

Optional components may also be added to either the first or second solvent being used to clean and flush, respectively, the bone graft, including but not limited to, antibiotics, antiviral agents (for example, peroxide generating agents such as Exact (a trademarked product marketed by ExOxEmis, Inc., San Antonio, Tex.)), hydrogen peroxide, permeation enhancers (for example, fatty acid esters such as laurate, myristate and stearate monoesters of polyethylene glycol), organic acids (for example, citric acid) or dilute solutions of strong acids (for example, hydrochloric acid).

III Cleaning of Small-Cut Bone Grafts

Cleaning of small bone grafts by the method of the present invention is accomplished by thawing of essentially intact bones. The bone is debrided of excess soft tissue using mechanical means, for example scalpels are used to cut away excess soft tissues, or the bone is exposed to basic solutions such as sodium hydroxide or trisodium phosphate and cut into appropriate/usable pieces using a commercially available bone saw, for example, a Stryker bone saw. Water lavage is used to break up and remove surface lipids and blood, and the cut-bone grafts are placed into the tank of an ultrasonic cleaner, for example, Branson models including 1210, 2210, 3210, 5210 or 8210, etc., in the presence of a solvent containing one or more detergents, for example, Allowash™ Solution at a concentration between 1X and 0.001X but preferably at 0.11X in sterile endotoxin-free deionized/distilled water as described in co-pending patent application No. 08/620,856 hereby incorporated by reference, or other appropriate detergent or combination of detergents with or without alcohol, and sonicated for about 10 to 120 minutes, preferably about 20 to 60 minutes and most preferably for about 30 minutes, at a temperature of from about 27° C. to 50° C., and more preferably at about 37° C. to 44° C. Preferably, the Ultrasonic cleaning devices operates in the range of 20 KHz to 50 KHz, more preferably 40 KHz to 47 KHz. Temperatures higher than about 50° C. provide for better cavitation, however, temperatures higher than 100° C. also tend to precipitate proteins present in the bone marrow maling them more difficult to remove from the cancellous bone space in the bone grafts.

The solvent containing detergent is then decanted/ removed and replaced with the second solvent, which may include but is not limited to sterile endotoxin free deionized/ distilled water solutions of antibiotics, hydrogen peroxide, antimycotics, antivirals, alcohol (for example ethanol or isopropanol), ion exchange resins, adsorbents, antioxidants, vitamins, growth factors, softeners, organic acids/bases, inorganic acids/bases and the like. The bone grafts in the second solvent are then: (a) washed using mild or vigorous agitation for a time period of about 5 to about 25 min, preferably for about 10 min, or (b) sonicated for about from 10 to about 120 min, preferably 20 to 60 min, and most preferably for about 10 min to 30 min at a temperature from about 27° C. to 50° C., and preferably from about 37° C. to 44° C.

The second solvent is then decanted and replaced with a third solvent, preferably sterile endotoxin-free deionized distilled water and (a) washed for about 5 to 25 minutes, preferably for about 10 to 20 minutes, with mild or vigorous agitation, or (b) sonicated for about from 10 to about 120 min, preferably 20 to 60 min, and most preferably for about 30 min at room temperature.

The third solvent is then decanted and replaced with a solution containing a decontaminating agent, for example, 3% hydrogen peroxide at room temperature, and: (a) soaked with mild or vigorous agitation for about 5 to 25 minutes, preferably for about 10 to 20 minutes, or (b) sonicated for about from 10 to about 120 min, preferably 20 to 60 min, and most preferably for about 30 min at room temperature. The bone grafts are then removed from the container, rinsed using water lavage and placed into alcohol, preferably 70% alcohol (isopropanol or ethanol) for a minimum of 15 minutes to a maximum of 24 hours. As a final wash, the bone grafts are washed using lavage; mild or vigorous agitation; or sonication, with sterile endotoxin-free deionized/distilled water and freeze-dried for packaging and distribution.

Any combination of sonicating and/or agitation is contemplated in the present method with the requirement that the first step comprise sonicating the bone graft, where subsequent processing steps may include agitation only, sonication only and agitation and sonication in any order.

The following examples illustrate processing of large and small bone grafts according to the instant invention.

EXAMPLE I

Figure 2:
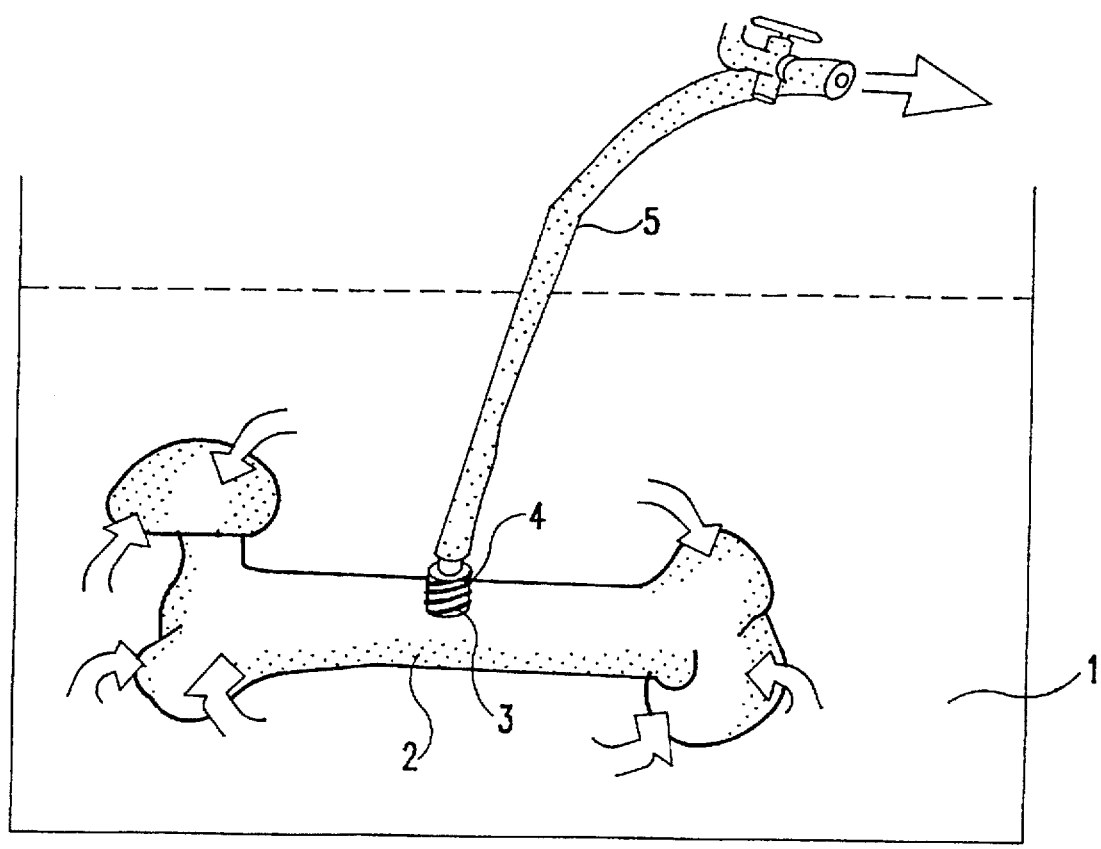
FIG. 2.
Figure 3:
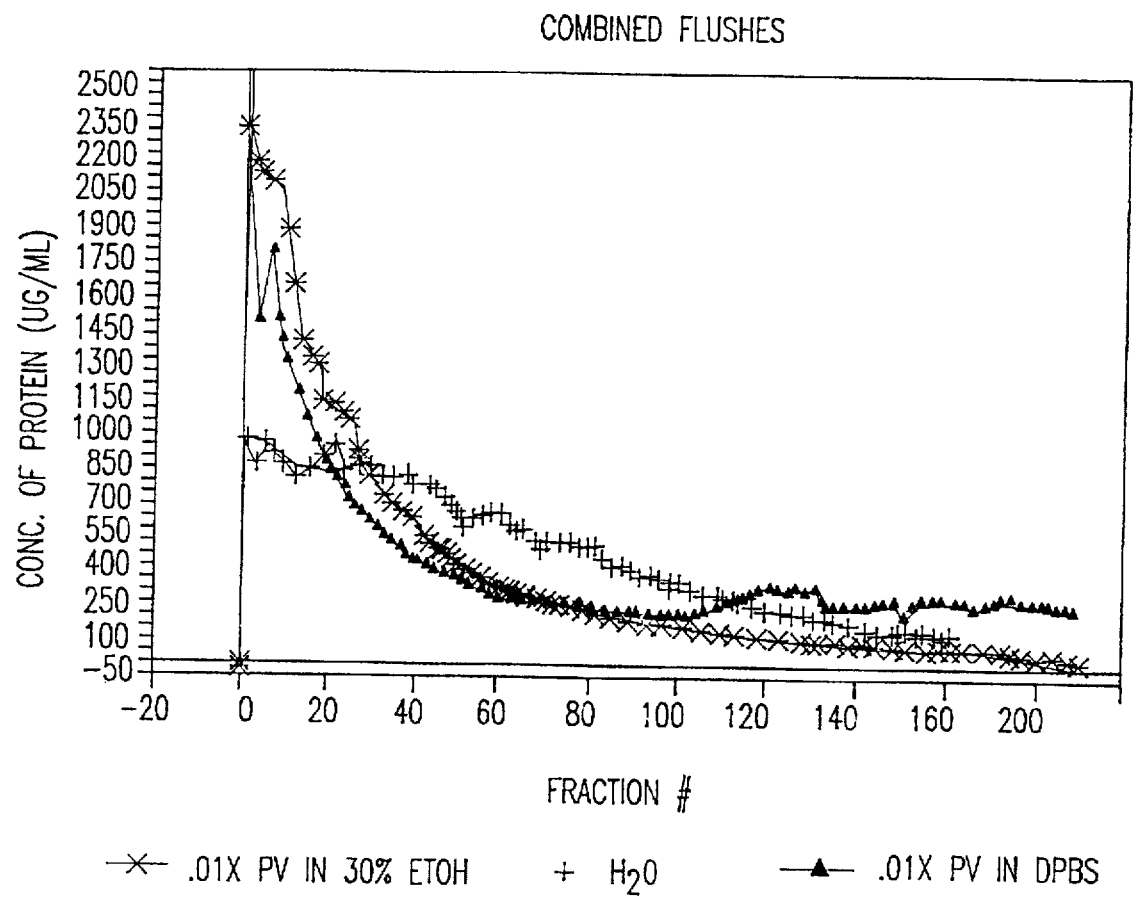
FIG. 3.

A femur is thawed, debrided of excess soft tissue (including the excess cartilage present on the articulating surfaces) and a hole (3) approximately ¼ to ⅝ inch outside diameter is drilled in the bone shaft approximately midway between the distal and proximal ends of the bone (2). The hole need only be drilled deep enough to penetrate the cortical bone such that the tapping port (4) (FIG. 2) may be securely inserted into the hole. The vacuum line (5) is attached securely to the tapping port. Two liters of a solution of 10% ethanol and Allowash™ Solution at a concentration of 0.01X are added to a container (1) designed to hold approximately 3 liters, for example the tank of a Branson ultrasonic cleaner model 2210 or 3210, and the bone graft with attached vacuum line is placed into the container, immersing it towards the bottom of the container. The temperature of the cleaning solution is adjusted to 45° C. prior to addition of the bone graft and the ultrasonic cleaner with bone graft is placed into a heated mode and the ultrasonic cleaner is turned on. Vacuum, 25 to 27 inches Hg, is applied to the system. The flow rate of solution through the bone graft is maintained at approximately 10 ml per minute by adjusting the vacuum. The solution collected in the disposable container is dark red(ish) initially, turning to a color similar to that of serum as bone marrow is removed from the graft. By sampling the effluent material being removed from the bone graft, via a sampling port accessible by use of a syringe, it is possible to monitor completion of bone marrow removal by measuring absorbance at 410 nm (See FIG. 3 for an example of changes in absorbance with volume of detergent (Panavirocide) drawn through a typical bone graft) it is possible to determine when essentially all of the bone marrow is removed from the bone graft. After drawing the two liters of solution through the bone graft the vacuum to the system is discontinued and the container is refilled with one 1 to 3 liters of endotoxin-free deionized/ distilled water and vacuum is reapplied to the system. The deionized/distilled water is drawn through the bone graft at approximately 15 mls per minute to remove the detergent solution. The ultrasonic bath may be turned on at this stage if the bone still retains a reddish color due to the presence of reduced bone marrow if desired, however, most of the bone marrow and bone marrow elements have already been removed from the bone. Following the removal of detergent solution from the bone graft, vacuum is discontinued to the system and the bone graft is removed from the container and the vacuum line and tapping port are removed. The bone graft is now ready for further processing into small bone grafts as required.

EXAMPLE II

Figure 4:
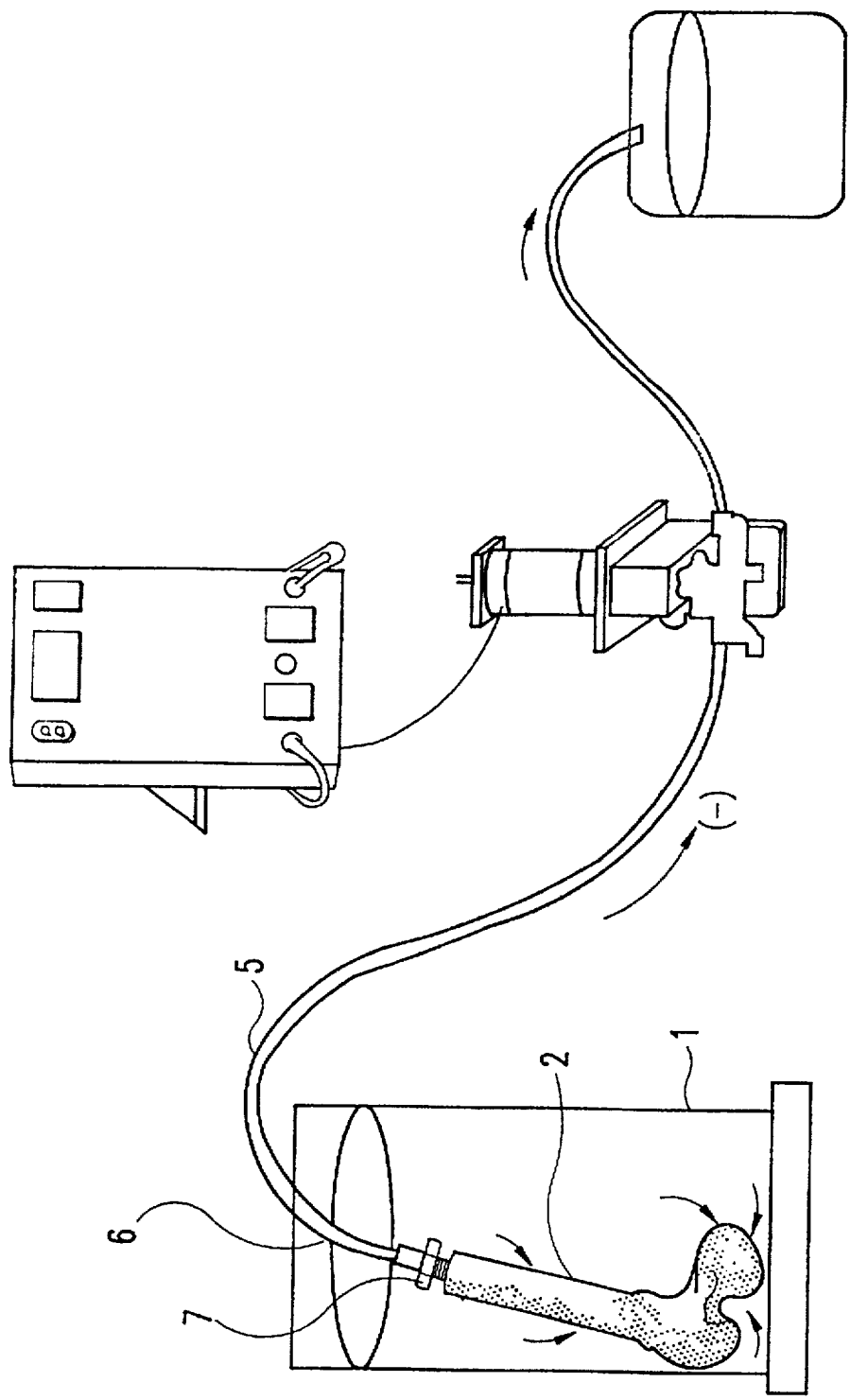
FIG. 4.

A femur is thawed, debrided of excess soft tissue (including the excess cartilage present on the articulating surfaces where desired) and cut in half using a bone saw. The proximal end of the femur (2) is used in this example, however, the distal end of the femur would be similarly processed. Pulsavac lavage or other mechanical means is used to remove bone marrow from the luminal space. One to three liter of a solution of Allowash™ Solution in sterile endotoxin-free deionized/distilled water, at a concentration of 0.01X, is added to a container (1) designed to hold approximately 1.5 to 3.0 liters, for example, the tank of an ultrasonic cleaner capable of operating at 40 to 47 kHz, and the bone graft is placed into the container, immersing it towards the bottom of the container. The vacuum line (5) is attached securely to the access line (6) in the sealing cap (7). (See FIG. 4 for an illustration of this assembly.) The temperature of the cleaning solution is adjusted to room temperature (approximately 27° C. prior to addition of the bone graft) and the container with bone graft is subjected to ultrasonic cleaning. Vacuum, in the range of 25 to 27 inches Hg, is applied to the system. The flow rate of solution through the bone graft is maintained at approximately 10 ml per minute by adjusting the vacuum. The drawn solution is collected in the disposable container and is dark red(ish) initially, turning to a color similar to that of serum as bone marrow is removed from the graft. By sampling the effluent material being removed from the bone graft, via a sampling port accessible by use of a syringe, it is possible to monitor completion of bone marrow removal by monitoring absorbance at 410 nm (See FIG. 3 for an example of changes in absorbance with volume of detergent (Allowash™ Solution) flushed through a typical bone graft.) It is possible to determine when essentially all of the bone marrow is removed from the bone graft. After drawing the one to three liters of solvent through the bone graft, or any volume necessary to completely remove the bone marrow as indicated by absorbance at 410 nm, the vacuum to the system is discontinued and the container is refilled with 1 to 3 liters of endotoxin-free deionized/distilled water and vacuum is reapplied to the system. The deionized/distilled water is drawn through the bone graft at approximately 15 mls per minute to remove the detergent solvent. Following the removal of detergent solvent from the bone graft, vacuum is discontinued to the system and the bone graft is removed from the container and the vacuum line and tapping port are removed. The bone graft is now ready for further processing into small bone grafts as required.

EXAMPLE III

A femur (2) is thawed, debrided of excess soft tissue (including the excess cartilage present on the articulating surfaces) and a hole (3) approximately ¼ to ⅜ inch outside diameter is drilled in the bone shaft approximately midway between the distal and proximal ends of the bone. The hole need only be drilled deep enough to penetrate the cortical bone such that the tapping port (4) (FIG. 2) may be securely inserted into the hole (3). The vacuum line (5) is attached securely to the tapping port (4). Four liters of a solution of 10% ethanol and Allowash™ Solution, at a concentration of 0.01X, are added to the container designed to hold approximately 3 liters and the bone graft with attached vacuum line is placed into the container (1), immersing it towards the bottom of the container. The container is preferably the tank of an ultrasonic cleaner capable of operating at 40 KHz to 47 KHZ. The temperature of the cleaning solution is adjusted to 45° C. prior to addition of the bone graft and the container with bone graft is subjected to ultrasonic cleaning. Vacuum, 25 to 27 inches Hg, is applied to the system. The flow rate of solution through the bone graft is maintained at approximately 10 ml per minute by adjusting the vacuum. The solution collected in the disposable container is dark red(ish) initially, turning to a color similar to that of serum as bone marrow is removed from the graft. By sampling the effluent material being removed from the bone graft, via a sampling port accessible by use of a syringe, it is possible to monitor completion of bone marrow removal by measuring absorbance at 410 nm (See FIG. 3 for an example of changes in absorbance with volume of detergent drawn through a typical bone graft.) it is possible to determine when essentially all of the bone marrow is removed from the bone graft. After drawing the two to four liters of solution through the bone graft or that volume necessary to completely remove the bone marrow as indicated by absorbance at 410 nm, the vacuum to the system is discontinued and the container is refilled with 1 to 3 liters of 3% hydrogen peroxide (vol:vol) in endotoxin-free deionized/distilled water and vacuum is reapplied to the system. The hydrogen peroxide deionized/distilled water solution is drawn through the bone graft at approximately 15 mls per minute to remove the detergent solution. Following the removal of detergent solution from the bone graft, vacuum is discontinued to the system and the bone graft is removed from the container and the vacuum line and tapping port are removed. The bone graft is now ready for further processing into small bone grafts as required.

EXAMPLE IV

Figure 5A:
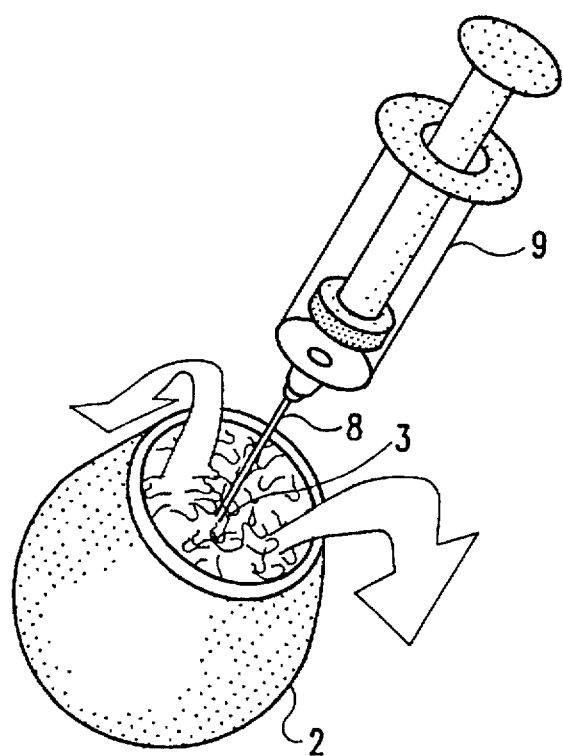
FIGS. 5 and 5A.
Figure 5:
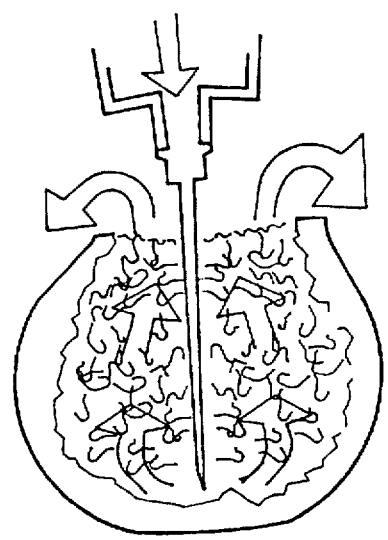

For cleaning smaller portions of an essentially intact bone graft, for example, femur heads, it is not necessary to use the larger containers, or the vacuum induced flow of flushing and/or washing solutions. Instead, a large volume syringe with an approximate 18 gauge needle may be used to cause a flow of solutions through the cancellous bone space in the smaller portions of whole bone grafts. In the cleaning process illustrated in FIG. 5, a femur head (2) is cut from the proximal end of a femur. A small hole (3) is drilled in the approximate center of the cut cross-sectional area to a depth approximating the beginning of the cortical bone distally to the point at which the hole is initiated. The diameter of the hole is drilled to be slightly smaller than the outside diameter of the needle (8), which is to be inserted. Once the needle is inserted, the bone graft is lowered into the tank of an ultrasonic cleaner, for example, a Branson model 1210, filled with cleaning solution, for example, a detergent solution consisting of 2 wt % Triton X-100, and the ultrasonic cleaner turned on prior to initiation of flow of cleaning solution which may be caused to occur by means of pressure applied on the syringe plunger in the syringe (9) or by use of a peristaltic pump attached to the needle inserted into the cancellous bone space of the small bone graft, for example, the femur head as illustrated in FIG. 5. The cleaning solutions utilized are equivalent to those described in previous examples given. Cleaning solutions may be removed from the cancellous bone space by attaching a fresh syringe to the needle or moving a solvent line attached to a peristaltic pump and flushing endotoxin-free ultra-pure water through the cancellous bone space. The volumes of cleaning solutions necessary to clean a typical femur head, as illustrated, may range from 200 mls to 500 mls with the preferred volume being 250 to 300 mls. The volumes of washing solutions necessary to remove residual cleaning solution from a typical femur head, as illustrated, may range from 50 mls to 200 mls, with the preferred volume being 100 to 150 mls.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims. Any references including patents and co-pending applications cited herein are incorporated herein in their entirety.

What is claimed:

1. A method for producing a bone graft suitable for transplantation into a human, comprising:

sonicating said bone graft with a solvent comprising one or more detergents in an ultrasonic cleaner at a temperature from 37° to 50° C. and for a time period effective to produce a cleaned bone graft essentially free from bone marrow.

2. A method for producing an essentially intact bone graft suitable for transplantation into a human, comprising:

sonicating said bone graft with a solvent comprising one or more detergents in an ultrasonic cleaner at a temperature and for a time period effective to produce a cleaned bone graft essentially free from bone marrow and, inducing a pressure mediated flow of said solvent through an opening in a bone shaft of said essentially intact bone graft wherein said pressure mediated flow is carried out for a period of time effective to produce a cleaned bone graft essentially free from bone marrow, and wherein said step of sonicating and said step of inducing are carried out simultaneously.

3. The method of claim 1, wherein said bone graft is an essentially intact bone graft or a small cut bone graft.

4. The method of claim 3, wherein said bone graft is an essentially intact bone graft, further comprising:

inducing a pressure mediated flow of said solvent through an opening in a bone shaft of said essentially intact bone graft, wherein said pressure mediated flow is carried out for a period of time effective to produce a cleaned bone graft essentially free from bone marrow, and wherein said step of sonicating and said step of inducing are carried out simultaneously.

5. The method of claim anyone of claims 4 or 2, wherein said flow is mediated at a positive pressure at or above 1 atmosphere, or said flow is mediated at a negative pressure below 1 atmosphere.

6. The method of claim 5, wherein said pressure mediated flow of solvent is conducted and effluent solvent is collected, in an essentially closed system.

7. An essentially intact bone graft produced by the process as claimed in claim 5.

8. The method of claim 1, wherein said temperature is in a range of from about 37° C. to about 44° C. and said time period is for about 30 minutes.

9. The method of claim 8, wherein said ultrasonic cleaner is operated in a range of from 40 to 47 KHZ.

10. A bone graft suitable for transplantation into a human, comprising the cleaned bone graft produced by the process as claimed in any one of claims 1, 8, or 9.

11. A method for producing a bone graft suitable for transplantation into a human, comprising:

sonicating at a temperature from 37° to 50° C. said bone graft using an ultrasonic cleaning device with a first solvent comprising one or more detergents to produce a first cleaned bone graft, and wherein said first cleaned bone graft is essentially free from bone marrow.

12. The method of claim 11, further comprising:

agitating said first cleaned bone graft with a second solvent comprising one or more members selected from the group consisting of: an antibiotic, an antimycotic and an antiviral agent, to produce a second cleaned bone graft; and agitating said second cleaned bone graft with a third solvent comprising one or more decontaminating agents to produce a third cleaned bone graft.

13. The method of claim 12, further comprising:

agitating said second cleaned bone graft with sterile water prior to sonication with said third solvent.

14. The method of claim 12 or 13 further comprising:

agitating said third cleaned bone graft with a fourth solvent comprising one or more alcohols to produce a fourth cleaned bone graft.

15. The method of claim 14, further comprising washing said forth cleaned bone graft with sterile water.

16. The method of claim 15, wherein said washing comprises: soaking, sonicating, lavage or agitation.

17. The method of claim 12, wherein said agitating comprises mild agitation.

18. The method of claim 12, wherein said agitating comprises vigorous agitation.

19. The method of claim 11, further comprising:

sonicating said first cleaned bone graft using an ultrasonic cleaning device with a second solvent comprising one or more members selected from the group consisting of: an antibiotic, an antimycotic and an antiviral agent, to produce a second cleaned bone graft; and sonicating said second cleaned bone graft using an ultrasonic cleaning device with a third solvent comprising one or more decontaminating agents to produce a third cleaned bone graft.

20. The method of claim 19, further comprising:

sonicating said second cleaned bone graft with sterile water prior to sonication with said third solvent.

21. The method of anyone of claims 19 or 20, further comprising:

sonicating said third cleaned bone graft with a fourth solvent comprising one or more alcohols to produce a fourth cleaned bone graft.

22. The method of claim 21, further comprising:

washing said fourth cleaned bone graft with sterile water.

23. A method for producing an essentially intact bone graft suitable for transplantation into a human, comprising:

inducing a negative pressure mediated flow of a first solvent, said first solvent comprising one or more detergents, through an opening in a bone shaft of said essentially intact bone graft to produce a cleaned intact bone graft;

sonicating said essentially intact bone graft in a container with said first solvent using an ultrasonic cleaner, wherein said inducing and said sonicating are carried out simultaneously for a time effective to produce a cleaned intact bone graft essentially free from bone marrow.

24. A method for producing a bone graft suitable for transplantation into a human, comprising:

sonicating said bone graft using an ultrasonic cleaning device with a first solvent comprising one or more detergents to produce a first cleaned bone graft;

sonicating said first cleaned bone graft using an ultrasonic cleaning device with a second solvent comprising one or more members selected form the group consisting of: an antibiotic, an antimycotic and an antiviral agent, to produce a second cleaned bone graft, and sonicating said second cleaned bone graft using an ultrasonic cleaning device with a third solvent comprising one or more decontaminating agents to produce a third cleaned bone graft, wherein said third cleaned bone graft is essentially free from bone marrow.

25. A method for producing a bone graft suitable for transplantation into a human, comprising:

sonicating said bone graft using an ultrasonic cleaning device with a first solvent comprising one or more detergents to produce a first cleaned bone graft;

agitating said first cleaned bone graft with a second solvent comprising one or more members selected from the group consisting of: an antibiotic, an antimycotic and an antiviral agent, to produce a second cleaned bone graft; and agitating said second cleaned bone graft with a third solvent comprising one or more decontaminating agents to produce a third cleaned bone graft, wherein said third cleaned bone graft is essentially free from bone marrow.

* * * * *

UNITED STATES PATENT AND TRADEMARK OFFICE
CERTIFICATE OF CORRECTION

PATENT NO. :5,797,871
DATED :August 25, 1998
INVENTOR(S) :Wolfinbarger, Jr.

It is certified that error appears in the above-identified patent and that said Letters Patent is hereby corrected as shown below:

Column 1, line 21, delete "Intact" and insert -- intact --
Column 1, line 28, delete "Coward" and insert -- cloward --.
Column 1, line 67, delete "Cryolite" and insert -- Cryolife --; and delete "Mariti" and insert -- Marietta --.
Column 2, line 7, delete "Cryolite" and insert -- Cryolife --
Column 13, line 49, delete "claim 12 or 13" and insert --anyone of claims 12 or 13--
Column 13, line 55, delete "forth" and insert -- fourth --
Column 12, line 57, delete "and," and insert -- , and --
Column 14, line 39, delete "form" and insert -- from --.

Signed and Sealed this

Ninth Day of March, 1999

*Attest:*

Q. TODD DICKINSON

*Attesting Officer*  *Acting Commissioner of Patents and Trademarks*

(12) EX PARTE REEXAMINATION CERTIFICATE (5517th)
United States Patent
Wolfinbarger, Jr.

(10) Number: US 5,797,871 C1
(45) Certificate Issued: Sep. 19, 2006

(54) ULTRASONIC CLEANING OF ALLOGRAFT BONE

(75) Inventor: Lloyd Wolfinbarger, Jr., Norfolk, VA (US)

(73) Assignee: Lifenet, Virginia Beach, VA (US)

Reexamination Request:
No. 90/006,199, Jan. 22, 2002

Reexamination Certificate for:
Patent No.: 5,797,871
Issued: Aug. 25, 1998
Appl. No.: 08/646,519
Filed: May 7, 1996

Certificate of Correction issued Mar. 9, 1999.

Related U.S. Application Data

(63) Continuation-in-part of application No. 08/646,520, filed on May 7, 1996, and a continuation-in-part of application No. 08/395,113, filed on Feb. 27, 1995, now Pat. No. 5,556,379, which is a continuation-in-part of application No. 08/293,206, filed on Aug. 19, 1994, now abandoned.

(51) Int. Cl.
*A61M 31/00* (2006.01)

(52) U.S. Cl. .......................... 604/49; 128/898; 623/16; 134/61

(58) Field of Classification Search .................. None
See application file for complete search history.

(56) References Cited

U.S. PATENT DOCUMENTS

| | | |
|---|---|---|
| 3,291,640 A | 12/1966 | Livingston |
| 3,640,295 A | 2/1972 | Peterson |
| 3,649,163 A | 3/1972 | McCusker |
| 3,937,236 A | 2/1976 | Runnells |
| 4,020,183 A | 4/1977 | Asculai et al. |
| 4,193,818 A | 3/1980 | Young et al. |
| 4,233,174 A | 11/1980 | Sheridan |
| 4,557,853 A | 12/1985 | Collins |
| 4,776,853 A | 10/1988 | Klement et al. |
| 4,801,299 A | 1/1989 | Brendel et al. |
| 4,874,137 A | 10/1989 | Chiba |
| 5,095,925 A | 3/1992 | Elledge et al. |
| 5,120,833 A | 6/1992 | Kaplan |
| 5,135,915 A | 8/1992 | Czarniecki et al. |
| 5,192,282 A | 3/1993 | Draenert |
| 5,333,626 A | 8/1994 | Morse et al. |
| 5,336,616 A | 8/1994 | Livesey et al. |
| 5,414,144 A | 5/1995 | Watanabe et al. |
| 5,494,784 A | 2/1996 | Hosaka et al. |
| 5,509,968 A | 4/1996 | Carr |

(Continued)

FOREIGN PATENT DOCUMENTS

| | | |
|---|---|---|
| CA | 540798 | 5/1957 |
| EP | 0360743 | 3/1990 |
| GB | 964545 | 7/1964 |

OTHER PUBLICATIONS

Angermann, P. & O.B. Jepsen. 1991. Procurement, Banking and Decontamination of Bone and Collagenous Tissue Allografts: Guidelines for infection control. *The Hospital Infection Society.* 159–69.

Asselmeier, M.A. R. B. Caspari, S. Bottenfield 1993. A review of allograft processing and sterilization techniques and their role in transmission of the human immunodeficiency virus. *The Am. J. of Sports Med.* 21(2):170–175.

Brown, J.S. An Ultrasonic Cleaning Bath in General Practice. *Practitioner* Apr. 8, 1988. 232: p. 377.

(Continued)

*Primary Examiner*—Manuel Mendez

(57) ABSTRACT

The present invention is directed to a method for cleaning cadaveric donor bone to produce bone grafts suitable for transplantation into a human, as well as the bone grafts produced thereby. The present method involves removing bone marrow potentially containing bacteria, virus or fungi, from the donor bone by sonicating the bone in a solvent containing one or more detergents to produce bone grafts essentially free from bone marrow, as well as bone grafts essentially free from any detectable bacterial, fungal, or viral contamination.

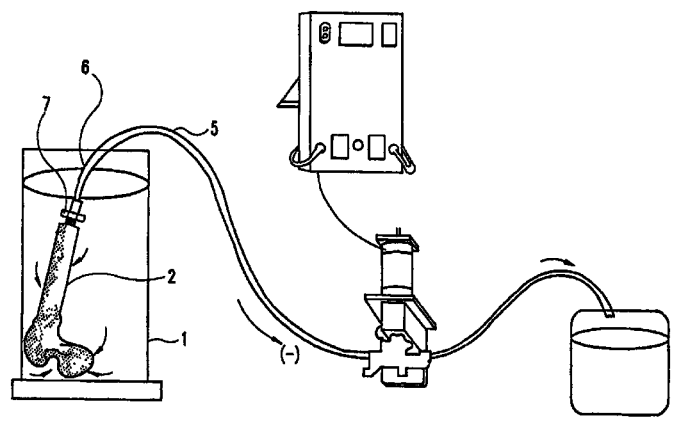

U.S. PATENT DOCUMENTS

| | | | |
|---|---|---|---|
| 5,539,043 | A | 7/1996 | Kimura et al. |
| 5,556,379 | A | 9/1996 | Wolfinbarger |
| 5,567,348 | A | 10/1996 | Nozawa et al. |
| 5,591,398 | A | 1/1997 | Knaepler et al. |
| 5,628,782 | A | 5/1997 | Myers et al. |
| 5,634,879 | A | 6/1997 | Mueller-Glauser et al. |
| 5,820,581 | A | 10/1998 | Wolfinbarger, Jr. |
| 5,976,104 | A | 11/1999 | Wolfinbarger, Jr. |
| 5,977,034 | A | 11/1999 | Wolfinbarger, Jr. |
| 6,024,735 | A | 2/2000 | Wolfinbarger, Jr. |
| 6,482,584 | B1 | 11/2002 | Mills et al. |
| 2003/0027125 | A1 | 2/2003 | Mills et al. |
| 2004/0037735 | A1 | 2/2004 | DePaula et al. |

OTHER PUBLICATIONS

Clarke, P.R. and C.R. Hill 1970. Physical and Chemical Aspects of Ultrasonic Disruption of Cells. *J. Acoust. Soc Amer.*, 472(2), Pt.2:649–53.

Helenius, A. & Simons, K. 1975 Solubilization of Membranes by Detergents. *Biochimica et Biophysica Acta* 415:29–79.

Horowitz B., R. Bonomo, A. M. Prince, S. N. Chin, B. Brotman, and R. W. Shulman 1992. Solvent/Detergent–Treated Plasma: A Virus–Inactivated Substitute for Fresh Plasma. *Blood.*79(3):826–31.

Hrazdira, I, 1965. Direct and Indirect Effect of Ultrasound on Bone Marrow Cell Suspensions. *Folia Biol.* (Prague) 11: 330–333.

Hughes, D.E. and W.L. Nyborg. 1962. Cell Disruption by Ultrasound. *Science* 138(3537):108–114.

Ribeiro, Anthony A., and Edward A. Dennis. 1973. Effect of Thermotropic Phase Transitions of Dipalmitoylphosphatidylcholine on the Formation of Mixed Micelles with Triton–X. *Biochimica et Biophysica Acta.* 332:26–35.

Shaw, C. A. 1982. Techniques Used in Excavation, Preparation, and Curation of Fossils From Rancho La Brea. *American Museum of Natural History* 25 (1):63–77.

Simonds, M.D. et al. Transmission of Human Immunodeficiency Virus Type 1 from a Seronegative Organ and Tissue Donor. *The New England Journal of Medicine.* Mar. 12, 1992. 726–732.

U.S. Appl. No. 09/213,224, filed Dec. 17, 1998, Wolfinbarger, Jr., abandoned.

Small, D.M. 1968. A Classification of Biologic Lipids Based upon Their Interaction in Aqueous Systems. *J. Am. Oil Chem. Soc.* vol. 45, pp. 108–119.

Birdi, K.S. 1975. Thermodynamics of Micelle Formation. *Colloidal Dispersions and Micellar Behavior* 233–238 (K.L. Mittal ed., Am. Chem Soc.).

Benton W. & H. Benton. 1981. Soaps and Detergents entry in *Encyclopedia Britannica* (16):914–15.

Detergency entry in *Encyclopedia of Chemical Technology* $4^{th}$ ed. (7):1072–1113 (not copied in its entirety) 1993.

Surfactants entry in *Encyclopedia of Chemical Technology* $4^{th}$ ed. (23):478–537 (not copied in its entirety) 1997.

Frederick, J. R. *Ultrasonic Engineering.* ch. 5, pp. 116–143; Ch. 8, pp. 308–316, 324, 325, 364, and 365. (J. Wiley & Sons, Press 1965).

Laughlin, R G. 1994. *The Aqueous Phase Behavior of Surfactants.* ch. 5, pp. 102–121.

Nagarajan, R. and E. Ruckenstein, Selective Solubilization in Aqueous Surfactant Solutions, *Surfactants in Solution,* vol. 2, 1984, pp. 923–947 (K.L. Mittal and B. Lindman, ed., Plenum Press, NY).

Porte, G. and J. Appell, The Sphere to Rod Transition of CPX and CTAX Micelles in High Ionic Strength Aqueous Solutions: the Specificity of Counterions. *Surfactants in Solution.* vol. 2, 1984. pp. 805–823 (K.L. Mittal and B. Lindman, ed., Plenum Press, NY).

U.S. Appl. No. 08/293,206, filed Aug. 14, 1994 by Wolfinbarger, L.

U.S. Appl. No. 08/395,113, filed Feb. 27, 1995 by Wolfinbarger, L.

1985. McCutcheon's Emulsifiers and Detergents. International Edition.

1985. McCutcheon's Functional Materials, North American Edition.

Lavelle et al. Dec. 1989. "Evaluation of an Antimicrobial Soap Formula For Virucidal Efficacy In Vitro Against Human Immunodeficiency Virus in a Blood–Virus Mixture." *Antimicrobial Agents and Chemotherapy.* vol. 33, No. 12.

Sharma et al. Oct. 1990. "An Antiviral Agent for General Use in Biological Samples and Tissue." *American Clinical Laboratory.* pp. 22–33.

1995. McCutcheon's Emulsifiers & Detergents. North American Edition and International Edition.

U.S. Appl. No. 08/293,206, filed Aug. 14, 1994, Wolfinbarger, Jr., abandonded.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–25 is confirmed.

* * * * *